United States Patent

Guay et al.

[11] Patent Number: 6,145,516
[45] Date of Patent: Nov. 14, 2000

[54] DENTAL HYGIENE ARTICLE

[75] Inventors: Gordon G. Guay, Chemlsford; Jean L. Spencer, Boston; Ronald R. Duff, Jr., Shrewsbury, all of Mass.

[73] Assignee: Gillette Canada Inc., Kirkland, Canada

[21] Appl. No.: 09/298,290

[22] Filed: Apr. 23, 1999

Related U.S. Application Data

[62] Division of application No. 08/772,891, Dec. 24, 1996, Pat. No. 5,941,256.

[51] Int. Cl.⁷ ............................................... A61C 15/00
[52] U.S. Cl. ............................................................. 132/321
[58] Field of Search ....................................... 132/321, 323

[56] References Cited

U.S. PATENT DOCUMENTS

| | | | |
|---|---|---|---|
| 2,748,781 | 6/1956 | Collat | 132/93 |
| 3,699,979 | 10/1972 | Muhler et al. | 132/89 |
| 3,942,539 | 3/1976 | Croliss et al. | 132/79 E |
| 3,943,949 | 3/1976 | Ashton . | |
| 4,033,365 | 7/1977 | Klepak et al. . | |
| 4,071,614 | 1/1978 | Grimm, III | 424/49 |
| 4,175,326 | 11/1979 | Goodson | 433/80 |
| 4,292,028 | 9/1981 | Barr | 433/180 |
| 4,348,378 | 9/1982 | Kosti | 424/7 |
| 4,459,277 | 7/1984 | Kosti | 424/7.1 |
| 4,597,959 | 7/1986 | Barr | 424/19 |
| 4,678,814 | 7/1987 | Rembaum | 522/175 |
| 4,780,320 | 10/1988 | Baker | 424/493 |
| 4,830,032 | 5/1989 | Jousson | 132/323 |
| 4,880,382 | 11/1989 | Moret et al. | 433/118 |
| 4,919,939 | 4/1990 | Baker | 424/493 |
| 4,941,487 | 7/1990 | VanBeneden | 132/323 |
| 4,971,785 | 11/1990 | Wilson et al. | 424/44 |
| 4,980,154 | 12/1990 | Gordon | 424/53 |
| 5,000,941 | 3/1991 | Chernack | 424/49 |
| 5,098,711 | 3/1992 | Hill et al. | 424/401 |
| 5,211,939 | 5/1993 | Turesky et al. | 424/49 |
| 5,250,288 | 10/1993 | Turesky et al. | 424/49 |
| 5,275,819 | 1/1994 | Amer et al. | 424/408 |
| 5,300,290 | 4/1994 | Spencer | 424/54 |
| 5,320,842 | 6/1994 | Spencer | 424/401 |
| 5,357,989 | 10/1994 | Gathani | 132/321 |
| 5,357,990 | 10/1994 | Suhonen et al. | 132/321 |
| 5,362,424 | 11/1994 | Lee et al. | 264/4.3 |
| 5,392,795 | 2/1995 | Gathani | 132/323 |
| 5,403,578 | 4/1995 | Gordon | 424/53 |
| 5,423,337 | 6/1995 | Ahlert et al. | 132/321 |
| 5,518,012 | 5/1996 | Dolan et al. | 132/321 |
| 5,732,721 | 3/1998 | Pelok | 132/321 |

FOREIGN PATENT DOCUMENTS

WO 93/15686   8/1993   WIPO .

*Primary Examiner*—Ralph A. Lewis
*Attorney, Agent, or Firm*—Fish & Richardson P.C.

[57] ABSTRACT

A dental hygiene article, including a dental floss, and a microcapsule associated with a portion of the floss. The microcapsule includes a pigment encapsulated within the microcapsule for changing the color of a portion of the floss associated with the microcapsule upon rupture of the microcapsule as an indication of use or release of an active agent.

41 Claims, 2 Drawing Sheets

DENTAL HYGIENE ARTICLE

CROSS REFERENCE TO RELATED APPLICATIONS

This application is a divisional application of Ser. No. 08/772,891, filed Dec. 24, 1996, now issued as U.S. Pat. No. 5,941,256.

BACKGROUND OF THE INVENTION

The invention relates to dental hygiene articles and more particularly to dental flosses that provide a visual indication of use of the floss or release of an active.

The most common way of minimizing the number of bacteria in the mouth is to brush and floss the teeth regularly. Dental floss is used to cleanse the interdental and subgingival regions of the mouth. Re-using the same section of floss, however, can result in moving food, bacteria and the like carried by the floss from one region to another rather than removing them entirely from the mouth. Although this is undesirable, it is often difficult to determine the sections of the floss that have already been used, which makes it difficult to avoid re-using sections of the floss. In addition, if the floss releases an active, re-using the same sections of floss decreases the amount of active delivered and accordingly diminishes the benefit derived from the floss.

SUMMARY OF THE INVENTION

In one aspect, the invention features a dental hygiene article including a dental floss, a microcapsule associated with a portion of the floss, and a pigment encapsulated within the microcapsule for changing the color of the portion of the floss associated with the microcapsule upon rupture of the microcapsule. Preferably the microcapsule is incorporated within the floss or provided on the surface of the floss.

In preferred dental hygiene articles, the microcapsule is pressure sensitive, i.e., the microcapsule walls are sufficiently thin that a force, such as the shear force applied while flossing, will cause the walls of the microcapsule to rupture thereby releasing the contents of the microcapsule. Preferred microcapsules will rupture under normal flossing forces.

In other preferred embodiments, the dental hygiene article further includes an active ingredient, i.e., a material capable of producing a desired effect within the mouth. Preferably the active ingredient is encapsulated within the microcapsule along with the pigment. The rupture of the pressure sensitive microcapsules allows the active ingredient to be introduced directly to a targeted tooth or gum area. This eliminates waste and increases accuracy of delivery of the active. In addition, pigment released from the microcapsules provides a visual indication to the user that the active has been released and the section of floss has been used, which prevents inadvertent re-use of floss that carries bacteria, etc., and/or is devoid of active. Suitable active ingredients include, e.g., flavorants, therapeutic agents, effervescing agents, and oils, e.g., an oil selected from the group that includes essential oils, flavor oils, scent oils, and oil soluble therapeutic agents, e.g., triclosan.

In one preferred embodiment, the pigment is dispersed in a liquid active ingredient within the microcapsule. Dispersing the pigment in the liquid active ingredient advantageously enables liquid active ingredients such as essential oils, scented oils, flavored oils, and oil soluble therapeutic agents to be incorporated directly into the microcapsule. This eliminates the need to apply flavor or scent in separate production steps and further eliminates the use of a non-active ingredient, e.g., mineral oil, as a separate dispersant.

In other preferred embodiments, the dental hygiene article may further include a second microcapsule associated with the floss. The second microcapsule preferably includes an active ingredient.

In another preferred embodiment, the dental hygiene article further includes, encapsulated within the microcapsule, a component selected from the group including a whitening agent, an anti-microbial agent (e.g., chlorhexidine), an anti-inflammatory agent, and an anti-calculus agent.

In other preferred embodiments, the microcapsule has an outer surface, and the dental hygiene article further includes an active ingredient associated with the outer surface. The microcapsule may have an tonically charged outer surface and a therapeutic agent having an ionic charge opposite the ionic charge of the outer surface adsorbed onto the outer surface of the microcapsule. In preferred embodiments, the therapeutic agent is an anti-microbial agent, more preferably chlorhexidine.

In one preferred embodiment, the dental hygiene article further includes a layer associated with the outer surface of the microcapsule. In preferred embodiments, the layer is impermeable to the active ingredient within the microcapsule, conceals the pigment within the microcapsule, or provides an tonically charged surface. Such a layer can help retain volatile compounds within the microcapsule and provide greater contrast when the pigment is released from the microcapsule. The layer may include an active ingredient.

In another aspect, the invention features a method of associating a microencapsulated pigment with a dental floss. In one preferred embodiment, the method includes applying the microencapsulated pigment to the surface of the dental floss. In another preferred embodiment, the method includes incorporating the microencapsulated pigment into the dental floss.

In still another aspect, the invention features a method of flossing an interdental region of a mammal including placing a portion of the above-described dental hygiene article in an interdental region, and flossing the region with the portion of the dental hygiene article.

The term "dental floss," as used herein, can mean any elongated flexible article used to cleanse the interdental and subgingival regions of the mouth including, for example, monofilament, multifilament and/or wax coated dental floss or dental tape.

The term "microcapsule," as used herein, refers to a hollow capsule having a diameter of less than about 2000 $\mu$m.

Other features and advantages of the invention will be apparent from the following description of the preferred embodiments thereof, and from the claims.

DESCRIPTION OF THE PREFERRED EMBODIMENTS

Figure 1:
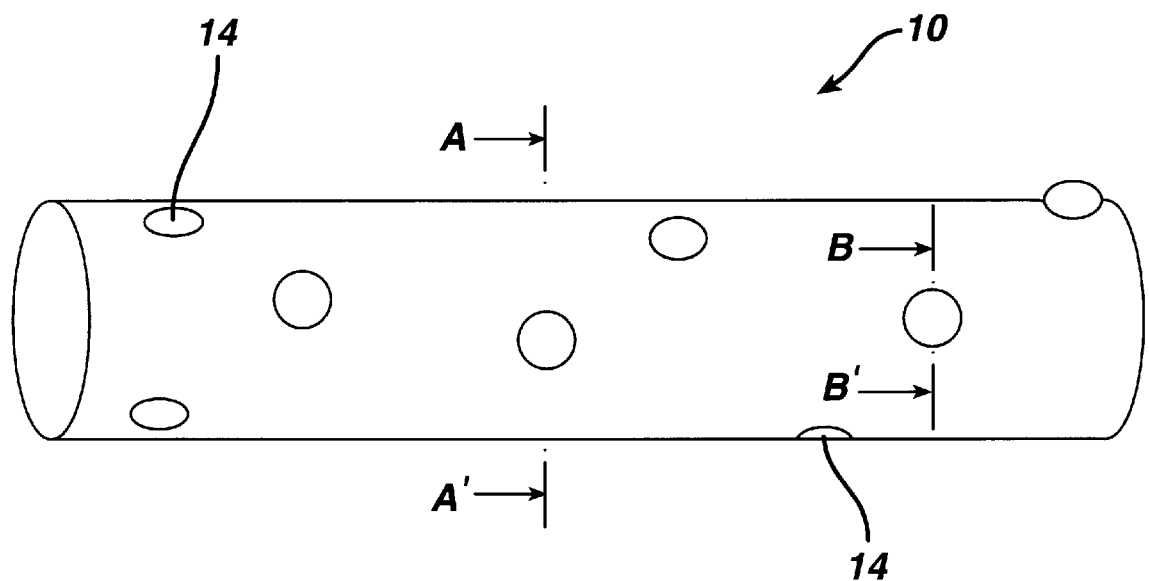
FIG. 1 is a side view of a segment of indicator floss.
Figure 2:
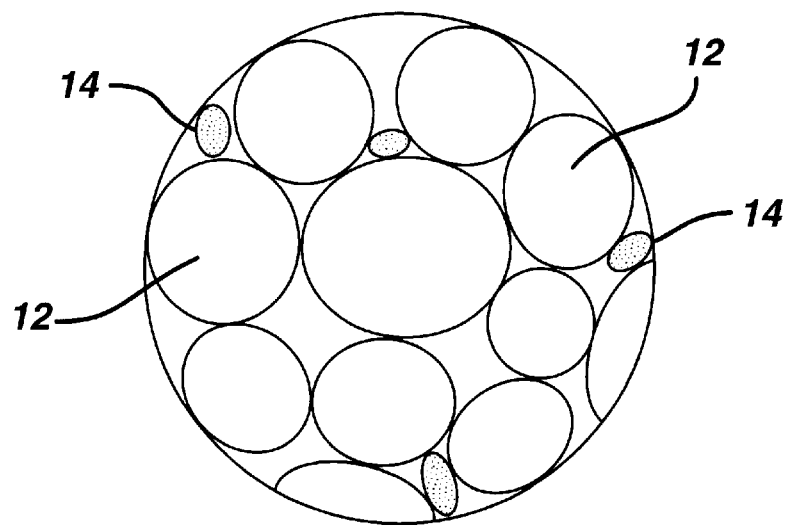
FIG. 2 is a cross-sectional view taken along line A—A' in FIG. 1.
Figure 3:
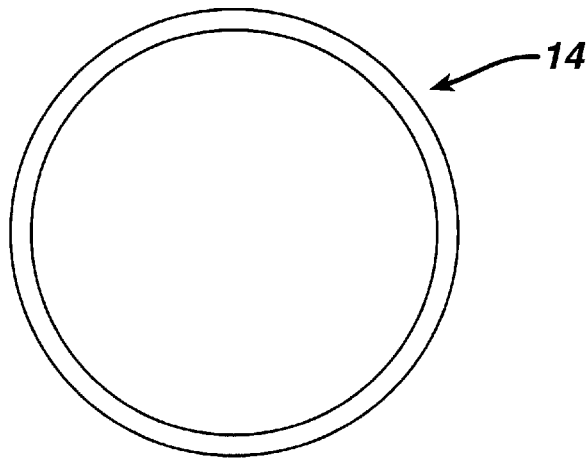
FIG. 3 is a highly enlarged cross-sectional view of a microcapsule taken along line B—B' in FIG. 1.

A preferred dental floss 10 of the present invention is shown in FIG. 1. A cross-section of the dental floss 10 of FIG. 1 is shown in FIG. 2. Dental floss 10 includes microcapsules 14 distributed randomly throughout the multiple filaments 12 of dental floss 10. An enlarged view of a cross-section of microcapsule 14 is shown in FIG. 3.

Microcapsules 14 contain a pigment and are designed to rupture during use of the floss causing a color change in a portion of the floss with which they are associated. This color change provides a visual indication to the user of the floss that the portion of floss has been used and the floss should either be discarded or a new section of floss should be used.

Any suitable material capable of forming a microcapsule may be used to form the encapsulating walls of the microcapsule, provided it is suitable for application in the mouth. Materials capable of forming microcapsules include, but are not limited to, the following: starch; dextrin; gelatin; gum arabic; casein; paraffin wax; natural waxes such as carnauba wax, beeswax, candelilla wax, Japan wax; styrene maleic acid; polyethylene-ethyl cellulose mixtures; cellulose acetophthalate; polymerized acrylonitrile; butadiene and styrene polymers; acetal copolymers and homopolymers; acrylic resins; allylic resins; amino resins; cellulosic resins; epoxy resins; fluoroplastic resins; Furan polymers; ionomer resins; nitrile barrier resins; nylon polymers; phenolic resins; phenylene-oxide based resins; poly (amide-imide) resins; polyaryl ethers; polyaryl sulfones; polybutadienes; polybutylenes; polycarbonates; polyesters; polyethersulfones; polyethylenes; polyamides; polyimides; polyphenylene sulfides; polypropylenes; polystyrenes; polysulfones; polyurethanes; polyvinyl polymers and resins; silicones; salts of heavy metal cellulose sulfates; gelatin derivatives of which gelatin is the main radical; poly (oxymethylene urea); melamine modified poly(oxymethylene urea); colloidal albumins; hydrolyzed polyvinyl acetate; hydrolysed cellulose esters, e.g., cellulose acetate hydrolysed to acetyl content of 19 to 26 percent; polyacrylamides; imidized polyacrylamides; polyvinyl alcohol; vinyl alcohol polymers containing urethane carboxylic acid groups, e.g., vinyl alcohol cyanoacetate vinyl copolymer; the polymer materials resulting from polymerizing proteins with monomers having a vinyl group; and naturally occurring and synthetic alginates, e.g., salts of water soluble heavy metals such as sodium, potassium and magnesium and combinations and mixtures thereof.

Preferred microcapsules are formed from materials including: starch, gelatin, xanthan gum, poly(oxymethylene urea), and melamine modified poly(oxymethylene urea). Starch, gelatin, and poly(oxymethylene urea) microcapsules are available from a number of sources, e.g., Lipo Technologies of Vadalia, Ohio, Ronald T. Dodge, Co. of Dayton, Ohio, and Minnesota Mining and Manufacturing of St. Paul, Minn. Suitable microcapsules may assume various shapes such as spherical, globular, kidney-like, and rice-like. Preferred microcapsules are spherical and have a diameter ranging from about 1 to about 1000 μm, more preferably less than about 100 μm.

Preferred microcapsules are pressure sensitive such that the walls of the microcapsule are thin enough to rupture upon the application of a shear force, e.g., the shear force exerted by flossing, yet of sufficient strength to withstand normally applied pressure occurring during manufacturing, handling and packaging of the dental hygiene article. Preferred microcapsules shear under normal flossing forces.

Methods of making pressure sensitive microcapsules include, polycondensation, interfacial polymerization, and coacervation/phase separation. These methods are well known in the art, and are disclosed, for example, in U.S. Pat. Nos. 3,472,675, 3,598,123, and 3,640,629.

Various methods may be used to apply the microcapsules to the floss including, for example, hot melt coating, resin bath coating, spray coating, lick roll coating, and web coating. In addition, the microcapsules may also be incorporated into the floss by various methods including, for example, coating the individual filaments that constitute a strand of floss prior to incorporating the filaments into the strand of floss. A binder, e.g., wax, can optionally be used to coat the floss with microcapsules. These methods are well known by those skilled in the art and are disclosed, for example, in U.S. Pat. No. 5,423,337.

Pigments suitable for encapsulation within the microcapsule include water insoluble pigments that are acceptable for use in the mouth, e.g., are non-toxic in the quantities that will be introduced to the mouth. Suitable pigments include synthetically derived pigments such as FD&C pigments, e.g., FD&C Blue #1 Lake, FD&C Blue #2 Lake, FD&C Yellow #5 Lake, FD&C Red #40 Lake; Erythrosin Lake; Amaranth Lake; Ponceau 4R Lake; Carmoisine Lake; natural pigments such as, e.g., titanium dioxide, Carmine Lake (blueish red), Carmine Lake (yellowish red), and Carmine Lake (purple); and pigments generated by converting a naturally derived dye to an aluminum or calcium-based salt.

Preferred pigments are those capable of changing the color of the dental floss, i.e., the pigment contained in the microcapsule is a color that is different from the color of the dental floss so that when the pigment is released from the microcapsule during flossing, the color change is visible to the naked eye. The change in color may be any visually observable color change, including a change of a white floss to another color; a change of a colored floss to white or another color; and a change in the intensity of the color of the floss.

The concentration of microencapsulated pigment in a unit area of the floss will affect the intensity of the color imparted to the used section of floss. Thus, the microencapsulated pigment is preferably present in the floss in a concentration sufficient to provide a visually observable color change when the pigment is released from the microcapsules. The amount of pigment required will vary depending on the pigment used, the concentration of the pigment in the microcapsules, the amount of microcapsules on the floss, and the payload of the microcapsules, and can be readily determined by those skilled in the art.

Many different components, singly or in any suitable combination, can be encapsulated within the microcapsule along with the color pigment or encapsulated within a second microcapsule. Suitable components and mixtures of components are those which are acceptable for use in the mouth, e.g., are non-toxic when provided in the amounts contemplated herein. These components can include, for example, therapeutic agents such as, e.g., anti-microbial agents, anti-gingivitis agents, anti-inflammatory agents, anti-caries agents, deodorizing agents, desensitizing agents, anti-calculus agents, anti-plaque agents, anti-viral agents, remineralization agents; nontherapeutic agents such as, e.g., effervescing agents, flavorants, scents, whitening agents, abrasives; and combinations thereof. The preferred concentration of additional components will vary depending on the intended function of the component and can be readily determined by the artisan.

Active ingredients such as flavor oils, essential oils, scent oils, and oil soluble therapeutic agents, e.g., triclosan, can be incorporated into the microcapsule to act as a carrier for the pigment. When the floss is used, the oils impart, e.g., flavor or scent to the floss while simultaneously functioning as a carrier of the pigment. Utilizing a scent, flavor oil, or oil soluble therapeutic agent as the pigment carrier instead of an inert oil eliminates the additional production steps of applying a scent, flavor, or therapeutic agent to the floss in a separate production step. This also eliminates the need for a carrier that serves no purpose other than to carry the pigment. Preferably the amount of pigment in a dispersion is about 1 to about 50% by weight pigment in oil, more preferably about 5 to about 10% by weight.

When a floss having microcapsules containing an active ingredient in addition to the pigment is used, the appearance or change of color of the floss not only indicates that the floss has been used but also indicates that the active ingredient has been released from a segment of the floss to a targeted area.

Suitable materials for use in forming filaments 12 of dental floss 10 are well known by those skilled in the art and include natural fibers, e.g., cotton and wool, synthetic polymer filaments, e.g., nylon, rayon, polyethylene, polyester, Dacron and acetate polymers, thermoplastic elastomers, e.g., Kratons (e.g., styreneethylene or styrene-butylene block copolymers), Pebax (e.g., polyether-polyamide block copolymers), and thermoplastic urethanes.

Figure 4:
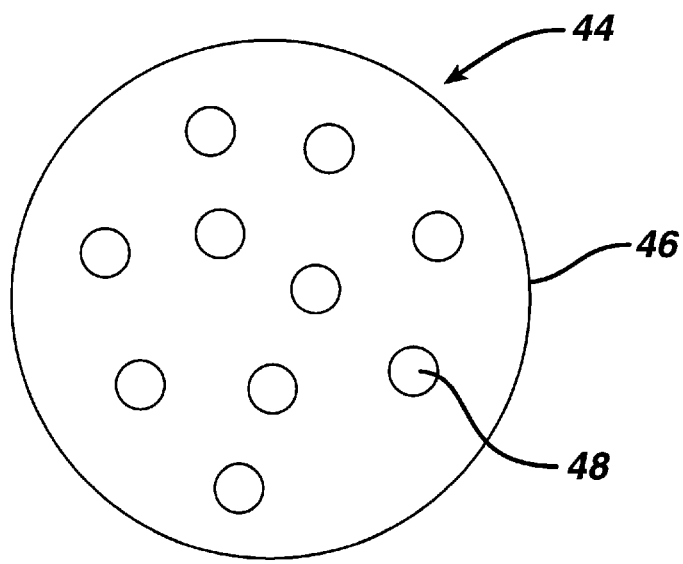
FIG. 4 is a highly enlarged schematic view of a microcapsule with active adsorbed onto the surface of the microcapsule.

In some embodiments, as shown in FIG. 4, microcapsules 44 are modified to have an tonically charged outer surface 46 onto which a therapeutic agent 48 such as an anti-microbial agent, having an ionic charge that is the opposite of the ionic charge of the outer surface, has been adsorbed. Methods of adsorbing anti-microbial agents onto the outer surface of microspheres are known in the art and are disclosed, for example, in U.S. Pat. No. 5,300,290 (Spencer) the disclosure of which is incorporated by reference herein. These methods would be suitable for adsorbing anti-microbial agents onto the outer surface of the microcapsules.

Any method that can produce a charged microcapsule is suitable for use in the present invention. Examples of suitable methods include those methods that produce a microcapsule that is inherently charged, charged as a result of chemical modification of the shell, charged as a result of inclusion of charged materials within the materials used to form the microcapsule, and combinations thereof. Such methods are well-known in the microencapsulation art. Methods for making charged microspheres are described, e.g., in Chung-Li et al., Progress in Colloid and Polymer Science, Vol. 60, pp. 163–175 (1976); Goodwin et al., Journal of Colloid and Polymer Science, Vol. 252, p. 464; and Goodwin et al., British Polymer Journal, Vol. 5, p. 347 (1973). These methods would be suitable to preparing the charged microcapsules. Examples of materials suitable for making charged microcapsules include carbon (negative charge); chromium hydroxide (positive or negative charge); clay (negative charge); and titanium dioxide (negative charge).

Preferably the anti-microbial agent is positively charged and the outer surface of the microcapsule has a negative charge. Suitable anti-microbial agents include, for example, bisbiguanides such as chlorhexidine and alexidine, which has a positive charge; bispyridines such as octenidine (positive charge); pyrimidines such as hexetidine (positive charge); quaternary ammonium ions such as cetylpyridinium, domiphen, benzalkonium, and benzethonium (all positively charged); alkaloids such as sanguinarine (positive charge); heavy metal ions such as zinc, stannous, and copper (all positively charged); surfactants such as lauryl sulfate, lauryl sarcosinate, and deoxycholate (all negatively charged); phenolic compounds such as eucalyptol, hexylresorcinol, menthol, methylsalicylate, phenol, 2-phyenylphenol, and thymol; antibiotics such as erythromycin, kanamycin, metronidazole, niddamycin, spyramycin, and tetracycline; enzymes such as amyolglucosidase, glucose oxidase, and mutanase, which include both positive and negative charges; and salts of chlorhexidine (e.g., the diacetate). Preferably the ionically charged anti-microbial agent is chlorhexidine.

Figure 5:
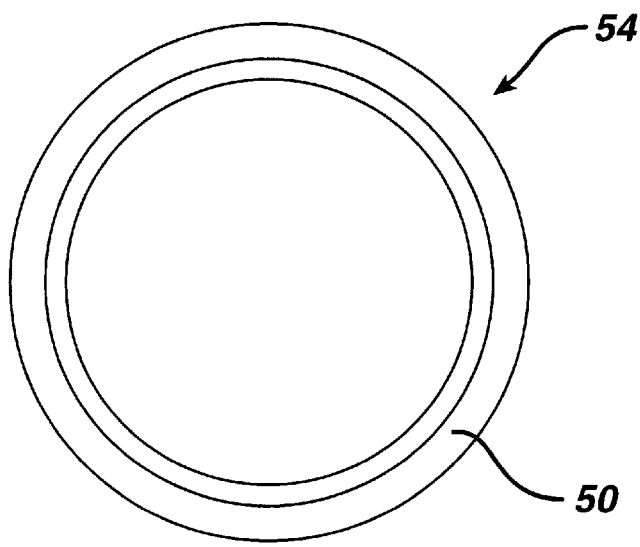
FIG. 5 is a highly enlarged schematic view of a microcapsule with a layer on the surface thereof.

In other embodiments, microcapsule 54 is modified to have a layer 50 on the outer surface of the microcapsule as shown in FIG. 5. Layer 50 surrounds a portion of the microcapsule, preferably the entire microcapsule. Layer 50 may conceal the color of the microcapsule or the pigment within the microcapsule. Suitable materials for concealing the color of the microcapsule or its contents include pigments, e.g., titanium dioxide coated as a powder onto the surface of the microcapsule. A suitable coating thickness of titanium dioxide is generally between about 1 $\mu$m to about 5 $\mu$m.

Suitable methods for applying a layer to a microcapsule include spray coating, spray drying, and vacuum coating. Preferably a second layer, e.g., a wax coating, is applied over the first layer to provide protection to the first layer during the manufacturing process.

Alternatively, or in addition, layer 50 may be impermeable, e.g., gas or liquid impermeable, to the component within the microcapsule. The impermeable layer inhibits loss of the component within the microcapsule due to evaporation or leaching. Preferably the impermeable layer inhibits loss of volatile active ingredients such as, e.g., flavor and scent oils. Materials suitable for forming impermeable layer 50 include, e.g., poly(methyl methacrylate), polystyrene, beeswax, carnauba wax, petroleum wax, polyethylene wax, paraffin wax, polyhydroxylalkanoic acid, glycolipids, glycerides, phospholipids, glycerol distearate, shellac (i.e., a complex mixture of aliphatic alicyclic hydroxy acid polymers), castor oil, chlorinated paraffin, cocoa butter, corn oil, ethylene glycol monostearate, lard, mineral oil, and hydrocolloids, e.g., starches, chemically modified starches, alginates, pectins, gum arabic, gelatin, casein, soy protein, whey protein, wheat gluten and zein. Suitable materials also include combinations of the above to form composite coatings including, e.g., a mixture of lipids and hydrocolloids, and a mixture of shellac and hydrocolloids.

The layer may also be ionically charged such that a therapeutic agent having an ionic charge that is opposite the ionic charge of the layer can be adsorbed onto the layer.

Layer 50 may also include an active ingredient. Suitable active ingredients include those active ingredients that are suitable for application in the mouth such as the active ingredients described above, that can be applied to the surface of the microcapsule, e.g., by spray coating, spray drying, vacuum coating, and that will remain adhered to the microcapsule until use of the portion of floss with which the microcapsule is associated. Preferably a second layer, e.g., a layer that is impermeable to the active ingredient, is applied over the surface of the layer of active ingredient to provide protection to the active ingredient during the manufacturing process.

Other embodiments are within the following claims. For example, although a multifilament dental floss has been described above, a monofilament dental floss can also be used. In addition, one of the components can be an agent that, when released from the microcapsule, will effervesce upon contact with the liquids in the mouth, e.g., sodium bicarbonate. Also, although uniform distribution of the microcapsules across the entire length of the floss is preferred, the microcapsules could be distributed in sections or other non-uniform distributions along a length of floss.

What is claimed:

1. A dental hygiene article comprising:
   a dental floss;
   a microcapsule disposed on a portion of said floss, said microcapsule having an outer surface and a layer disposed on said outer surface of said microcapsule; and
   a material on the layer of the microcapsule configured to adhere the microcapsule to the portion of the floss.
2. The article of claim 1, wherein said microcapsule contains an active ingredient.
3. The article of claim 2, wherein said layer is impermeable to said active ingredient.
4. The article of claim 1, wherein said layer comprises an active ingredient.
5. The article of claim 4, wherein said active agent is selected from the group consisting of a whitening agent, an anti-microbial agent, an anti-inflammatory agent, an anti-calculus agent, and combinations thereof.
6. The article of claim 1, wherein said layer comprises a pigment.
7. The article of claim 1, wherein said layer conceals the contents within said microcapsule.
8. The article of claim 1, wherein said layer comprises titanium dioxide.
9. The article of claim 8, wherein said layer comprises an active ingredient.
10. The article of claim 1, wherein said microcapsule comprises a pressure sensitive microcapsule.
11. The article of claim 1, wherein said microcapsule is constructed to release its contents upon the application of force to said floss.
12. The article of claim 1, further comprising an active ingredient encapsulated within said microcapsule.
13. The article of claim 12, wherein said active ingredient comprises an oil.
14. The article of claim 13, wherein said oil is selected from the group consisting of essential oils, flavor oils, scent oils, and oil soluble therapeutic agents.
15. The article of claim 12, wherein said active ingredient is in the form of a liquid.
16. The article of claim 1, further comprising a second microcapsule associated with said floss, said second microcapsule comprising an active ingredient.
17. The article of claim 1, further comprising, encapsulated within said microcapsule, a component selected from the group consisting of a whitening agent, an anti-microbial agent, an anti-inflammatory agent, an anti-calculus agent, and combinations thereof.
18. The article of claim 17, wherein said anti-microbial agent comprises chlorhexidine.
19. The article of claim 1, further comprising a therapeutic agent encapsulated within said microcapsule.
20. The article of claim 1, further comprising a second microcapsule associated with said dental floss, said second microcapsule comprising a therapeutic agent encapsulated therein.
21. The article of claim 1, further comprising an effervescing agent encapsulated within said microcapsule.
22. The article of claim 1, further comprising a second microcapsule associated with said dental floss, said second microcapsule comprising an effervescing agent encapsulated therein.
23. The article of claim 1, wherein said microcapsule is incorporated within said floss.
24. The article of claim 1, wherein said microcapsule is provided on the surface of said floss.
25. The article of claim 1, wherein said microcapsule comprises an abrasive.
26. The article of claim 1, wherein said layer comprises an abrasive.
27. The article of claim 1, further comprising a plurality of microcapsules having a layer disposed on the outer
   said article comprising a dental floss, a microcapsule associated with a portion of said floss, and a material on the layer of the microcapsule configured to adhere the microcapsule to the portion of the floss,
   said microcapsule comprising an outer surface and a layer disposed on said outer surface of said microcapsule; and
   flossing said region with said portion of said dental hygiene article.
28. A method of manufacturing a dental hygiene article comprising applying a microcapsule to a dental floss with a material configured to adhere the microcapsule to the floss, wherein the microcapsule comprising an outer surface and a layer disposed on said outer surface.
29. A method of flossing an interdental region of a mammal comprising:
   placing a portion of a dental hygiene article in an interdental region,
   said article comprising a dental floss, a microcapsule associated with a portion of said floss, and a material on the layer of the microcapsule configured to adhere the microcapsule to the portion of the floss,
   said microcapsule comprising an outer surface and a layer disposed on said outer surface of said microcapsule; and
   flossing said region with said portion of said dental hygiene article.
30. A dental hygiene article comprising:
   a dental floss;
   a microcapsule disposed on a portion of said floss, said microcapsule having an outer surface and a layer disposed on said outer surface of said microcapsule; wherein the layer comprises an active ingredient.
31. The article of claim 30, wherein said active agent is selected from the group consisting of a whitening agent.
32. The article of claim 30, wherein said active agent is selected from the group consisting of an anti-microbial agent.
33. The article of claim 30, wherein said active agent is selected from the group consisting of an anti-inflammatory agent.
34. The article of claim 30, wherein said active agent is selected from the group consisting of an anti-calculus agent.
35. The article of claim 30, wherein said active agent is selected from the group consisting of a whitening agent, an anti-microbial agent, an anti-inflammatory agent, an anti-calculus agent, and combinations thereof.
36. A dental hygiene article comprising:
   a dental floss;
   a microcapsule disposed on a portion of said floss, said microcapsule having an outer surface and a layer disposed on said outer surface of said microcapsule; wherein the layer comprises a pigment to conceal the contents within said microcapsule.

37. The article of claim 36, wherein the pigment comprises titanium dioxide.

38. The article of claim 36, further comprising an active ingredient encapsulated within said microcapsule.

39. The article of claim 38, wherein said active ingredient comprises an oil.

40. The article of claim 39, wherein said oil is selected from the group consisting of essential oils, flavor oils, scent oils, and oil soluble therapeutic agents.

41. The article of claim 38, wherein said active ingredient is in the form of a liquid.

* * * * *

UNITED STATES PATENT AND TRADEMARK OFFICE
CERTIFICATE OF CORRECTION

PATENT NO.   : 6,145,516
DATED        : November 14, 2000
INVENTOR(S)  : Ronald R. Duff, Jr., Gordon G. Guay and Jean L. Spencer It is certified that error appears in the above-identified patent and that said Letters Patent is hereby corrected as shown below:

Title Page, under Inventor:
Column 1,
Delete "Chemlsford" and insert --Chelmsford--

Under References Cited:

Column 1,
3,943,949 3/1976, insert --et al.......... 132/89-- after "Ashton"
4,033,365 7/1977, insert --............... 132/89-- after Klepak et al."

Column 2,
delete "5,357,989" and insert --5,359,999--

Column 8, Claim 27,
Lines 11-20, Delete "said article comprising a dental floss, a microcapsule associated with a portion of said floss, and a material on the layer of the microcapsule configured to adhere the microcapsule to the portion of the floss, said microcapsule comprising an outer surface and a layer disposed on said outer surface of said microcapsule; and flossing said region with said portion of said dental hygiene article"
and, Insert --surfaces of said microcapsules, said microcapsules being distributed in sections along a length of said floss-

UNITED STATES PATENT AND TRADEMARK OFFICE
CERTIFICATE OF CORRECTION

PATENT NO.   : 6,145,516
DATED        : November 14, 2000
INVENTOR(S)  : Ronald R. Duff, Jr., Gordon G. Guay and Jean L. Spencer It is certified that error appears in the above-identified patent and that said Letters Patent is hereby corrected as shown below:

and, Insert --surfaces of said microcapsules, said microcapsules being distributed in sections along a length of said floss--

Signed and Sealed this

Nineteenth Day of June, 2001

*Attest:*

*Attesting Officer*

NICHOLAS P. GODICI
*Acting Director of the United States Patent and Trademark Office*